United States Patent
Jang

(10) Patent No.: US 10,750,995 B2
(45) Date of Patent: Aug. 25, 2020

(54) PAIN MONITORING AND FEEDBACK SYSTEM FOR DENTAL PROCEDURES

(71) Applicant: Wonseok Jang, Millburn, NJ (US)

(72) Inventor: Wonseok Jang, Millburn, NJ (US)

( * ) Notice: Subject to any disclaimer, the term of this patent is extended or adjusted under 35 U.S.C. 154(b) by 99 days.

(21) Appl. No.: 16/208,800

(22) Filed: Dec. 4, 2018

(65) Prior Publication Data

US 2020/0170572 A1   Jun. 4, 2020

(51) Int. Cl.
*A61B 5/00* (2006.01)
*A61B 5/01* (2006.01)
*A61B 5/11* (2006.01)
*A61B 5/22* (2006.01)
*A61C 19/08* (2006.01)

(52) U.S. Cl.
CPC .......... *A61B 5/4824* (2013.01); *A61B 5/0077* (2013.01); *A61B 5/01* (2013.01); *A61B 5/1107* (2013.01); *A61B 5/0002* (2013.01); *A61B 5/225* (2013.01); *A61B 5/7275* (2013.01); *A61C 19/08* (2013.01)

(58) Field of Classification Search
CPC ....... A61B 5/4824; A61B 5/0077; A61B 5/01; A61B 5/1107; A61B 5/0002; A61B 5/225; A61B 5/7275; A61C 19/08
See application file for complete search history.

(56) References Cited

U.S. PATENT DOCUMENTS 6,929,607 B2 * 8/2005 Lipman ................ A61B 5/4824
600/300

FOREIGN PATENT DOCUMENTS

| JP | 2005-103048 A | 4/2005 |
| JP | 2012-196238 A | 10/2012 |
| KR | 10-1263184 B1 | 5/2013 |

* cited by examiner

*Primary Examiner* — George Manuel
(74) *Attorney, Agent, or Firm* — Patent Office of Dr. Chung Park

(57) ABSTRACT

A pain monitoring and feedback system for dental procedures includes: a sensing device for taking a picture of a patient for the muscle change detection of the patient undergoing dental procedures, a heat-sensing unit for sensing the body temperature change of the patient, and a grip force-sensing unit for measuring the grip force of the patient; and a computing device for receiving data from the sensing device and outputting a signal corresponding to pain information, a control unit for analyzing at least one of the muscle change, the body temperature change and the grip force change of the patient by using the monitoring data received via the communication unit so as to estimate the pain of the patient and outputting a pain signal or controlling a procedure device according to the estimated pain, and a memory for storing data necessary for processing the control unit.

6 Claims, 3 Drawing Sheets

PAIN MONITORING AND FEEDBACK SYSTEM FOR DENTAL PROCEDURES

BACKGROUND OF THE INVENTION

Field of the Invention

The present invention relates to a pain monitoring and feedback system for dental procedures, in which the pain of a patient undergoing dental procedures can be monitored and the results can be fed back to the physician, and a method thereof.

Background Art

One of the biggest reasons why a patient is afraid of dental care and avoids it is pain. If there is pain during dental treatment, anesthesia is usually performed before the procedure. However, the degree that the anesthesia takes effect varies depending on a person, and the time required for recovering from the anesthesia is also different. Therefore, it is common to check if the anesthesia is achieved by communicating with a patient, and raise the hand and inform the doctor if the anesthesia is relieved and pain is felt.

However, there is a limitation in this communication in the case of patients who are children or elderly, or have mental or physical disabilities. For example, a patent who has difficulty in immediate communication may take time to inform a doctor who is concentrating on the procedure of the pain even if he or she feels severe pain. If a patent has this experience, the patient will be more afraid of coming to the dentist and avoid periodic dental examinations in the future, letting the related diseases progress.

If the patient is confident that he or she can stop the procedure immediately when there is pain, this fear can be reduced and the patient can prevent or treat the trauma of dental procedures.

Conventionally, there are methods for displaying the pain experienced by a patient as data, such as an electrocardiogram for monitoring changes in the heart condition, an electroencephalogram for monitoring the brain waves, and the like. However, the devices for performing these methods are usually expensive and there is a need to attach elements for detecting radio waves to parts of the patient's body. In addition, when these devices are attached to the body, the patient feels more uncomfortable and feels anxiety about the treatment. Therefore, these methods are difficult to be employed in dental procedures.

SUMMARY OF THE INVENTION

Technical Problem

Accordingly, the present invention has been made to solve the above mentioned problems occurring in the prior art, and thus the present invention has an objective to provide a system for monitoring the pain of a patient without any equipment attached to the body of the patient and providing feedback to a user when the patient feels pain.

Technical Solution

To accomplish the above objective, a pain monitoring and feedback system for dental procedures, according to an embodiment of the present invention, may include: a sensing device including a photographing unit for taking a picture of a patient for the muscle change detection of the patient undergoing dental procedures, a heat-sensing unit for sensing the body temperature change of the patient, and a grip force-sensing unit for measuring the grip force of the patient; and a computing device including a communication unit for receiving data from the sensing device and outputting a signal corresponding to pain information to the outside, a control unit for analyzing at least one of the muscle change, the body temperature change and the grip force change of the patient by using the monitoring data received via the communication unit so as to estimate the pain of the patient and outputting a pain signal or controlling a procedure device according to the estimated pain, and a memory for storing data necessary for processing the control unit.

The control unit determines whether to operate in a priority mode or a normal mode according to set mode information, and determines priorities of the muscle change, the body temperature change, and the grip force change so as to reflect the muscle change, the body temperature change, and the grip force change in pain determination, wherein the priorities are determined according to the input of a user in the case of operation in the priority mode and according to the preset information in the case of operation in the normal mode.

The control unit may set threshold values for the muscle change, the body temperature change, and the grip force change, and determine whether the pain of the patient is equal to or greater than a pain threshold value by using the data received from a monitoring unit, the determined priorities, and the set threshold values.

The control unit may output at least one of a notification signal for informing of the pain by an output device and a control signal for stopping the dental procedure device, when it is determined that the pain of the patient is equal to or greater than the preset pain threshold value.

A pain monitoring and feedback system for dental procedures, according to another embodiment of the present invention, may include the steps of: receiving monitoring data from a photographing unit for taking a picture of a patient for the muscle change detection of the patient undergoing dental procedures, a heat-sensing unit for sensing the body temperature change of the patient, and a grip force-sensing unit for measuring the grip force of the patient; analyzing at least one of the muscle change, the body temperature change and the grip force change of the patient by using the monitoring data so as to estimate the pain of the patient; and outputting a pain signal according to the estimated pain or outputting a control signal for controlling a procedure device.

Effect of the Invention

According to the present invention, the pain of a patient is monitored by analyzing the information received from a camera, a temperature sensing device, a grip force-sensing device, and the like without attaching any equipment to the body of the patient, and a feedback signal can be sent by an output device or procedure equipment.

In addition, according to the present invention, the patient does not have to feel the inconvenience of attaching any equipment to the body, and the fear of dental procedures can be reduced because the patient recognizes that the procedure is stopped immediately when feeling pain.

Furthermore, according to the present invention, since a doctor can detect the pain of a patient without the need to communicate with the patient or pay close attention to the patient, the doctor can concentrate on the procedure.

BRIEF EXPLANATION OF REFERENCE NUMERALS

Figure 1:
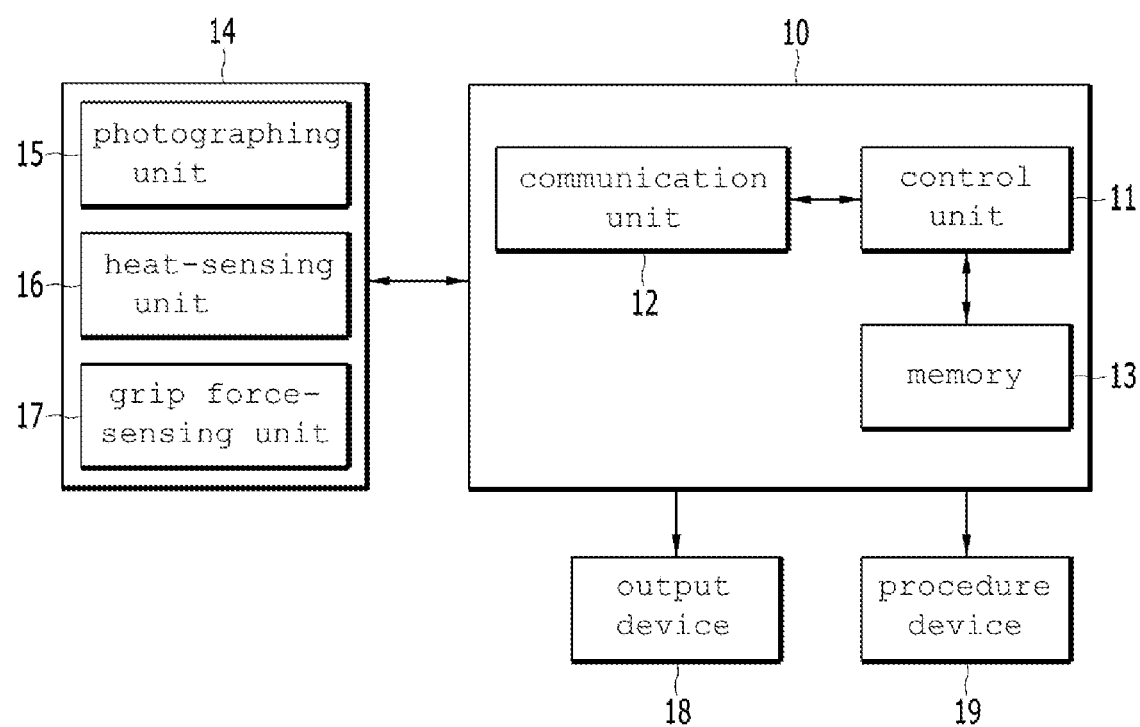
FIG. 1 is a diagram illustrating the configuration of a pain monitoring and feedback system for dental procedures according to an embodiment of the present invention.

10: computing device
11: control unit
12: communication unit
13: memory
14: sensing device
15: photographing unit
16: heat-sensing unit
17: grip force-sensing unit
18: output device
19: dental procedure device

DETAILED DESCRIPTION OF THE PREFERRED EMBODIMENT

The terms used in this specification will be briefly described, and the present invention will be described in detail. The terms used in the present invention are selected from the general terms that are widely used while taking into account the functions in the present invention, but may vary depending on the intentions of the skilled person in the art or precedents, the emergence of new technologies, and the like. In addition, in certain cases, there may be terms arbitrarily selected by the applicant, and the meaning thereof will be described in detail in the corresponding description of the invention. Therefore, the terms used in the present invention should be defined based on the meaning of the terms, not on the simple names of the terms, but on the entire contents of the present invention.

Whenever a component is referred to "include" any component throughout the specification, it is to be understood that the component may include other components and does not exclude any other component, unless specifically stated otherwise. Also, the terms " . . . means", " . . . part", " . . . module" and the like mean units that process at least one function or operation, which may be implemented in hardware or software, or a combination thereof.

Hereinafter, embodiments of the present invention will be described in detail with reference to the accompanying drawings in such a way that it can be easily carried out by a person skilled in the art, to which the present invention belongs. The present invention may, however, be embodied in many different forms and should not be construed as limited to the embodiments set forth herein. In order to clearly illustrate the present invention, parts not related to the description are omitted, and like parts are denoted by like reference numerals throughout the specification.

FIG. 1 is a diagram for explaining the configuration of a pain monitoring and feedback system for dental procedures according to an embodiment of the present invention.

Referring to FIG. 1, a pain monitoring and feedback system for dental procedures may include a sensing device 14 for sensing the muscle change, the body temperature change and the grip force change of a patient undergoing dental procedures, and a computing device 10 for determining whether the patient feels pain by using the data transmitted by the sensing device 14 and informing a user (doctor) of the pain feeling or temporarily stopping a procedure device 19 if it is determined that the patient feels pain.

The sensing device 14 includes a plurality of sensing units for sensing muscle change, body temperature change, and grip force change, respectively, and the plurality of sensing units include a photographing unit 15, a heat-sensing unit 16, and a grip force-sensing unit 17. The sensing units used in the present invention are not attached to the body of a patient, wherein the photographing unit 15 and the heat-sensing unit 16 among them are disposed away from the patient's body and the grip force-sensing unit 17 is held in hand by the patient.

The photographing unit 15 can be implemented using a camera to photograph the patient's body for the detection of the muscle change of the patient undergoing dental procedures, wherein the photographing unit 15 continuously captures the state of the patient undergoing dental procedures according to a control signal of the control unit 11 and returns the captured images to the control unit 11 as monitoring data.

The heat-sensing unit 16 can be implemented using a thermal camera or a heat-sensing device for sensing the body temperature of a patient undergoing dental procedures, wherein the heat-sensing unit 16 continuously measures the body temperature of the patient undergoing dental procedures according to a control signal of the control unit 11 and returns the monitoring data generated as a result of the measurement.

The grip force-sensing unit 17 can be implemented using a dynamometer in the form that a patient in the dental procedures can grasp by hand, wherein the grip force-sensing unit 17 continuously measures the grip force of the patient undergoing dental procedures according to a control signal of the control unit 11 and returns the monitoring data generated as a result of the measurement.

The computing device 10 receives the monitoring data from the photographing unit 15, the heat-sensing unit 16 and the grip force-sensing unit 17, and may include a communication unit 12 for transmitting a signal output from the control unit 11 to an external device, a control unit 11 for analyzing the monitoring data including the images, body temperature information, and grip force information 11 of a patient, and a memory 13 for storing the data required for processing the control unit 11.

The control unit 11 estimates the pain of the patient by analyzing at least one of the patient's muscle change, body temperature change, and grip force change by using the monitoring data received via the communication unit 12, and outputs a pain signal by an output device 18 or controls the procedure device 19 according to the estimated pain.

The output of the pain signal or the transmission of a control signal for controlling the procedure device 19 can also be performed via the communication unit 12. The communication unit 12 may include one or more communication modules for exchanging data with the photographing unit 15, the heat-sensing unit 16, the grip force-sensing unit 17, the output device 18, and the procedure device 19, wherein there is no restriction on the communication standard used herein, and any standard required for communication with an external device such as Bluetooth can be used.

The output device 18 is intended to inform the user (doctor) whether the patient feels pain as well as how much pain the patient feels, wherein the output device 18 may include at least one of a monitor, a speaker, and a vibration device, and may be physically implemented as part of the computing device 10 or the procedure device 19, depending on the embodiment.

The procedure device 19 is the device that the user uses for the dental procedures of the patient and can be converted into a paused state according to the control signal of the control unit 11.

Figure 2:
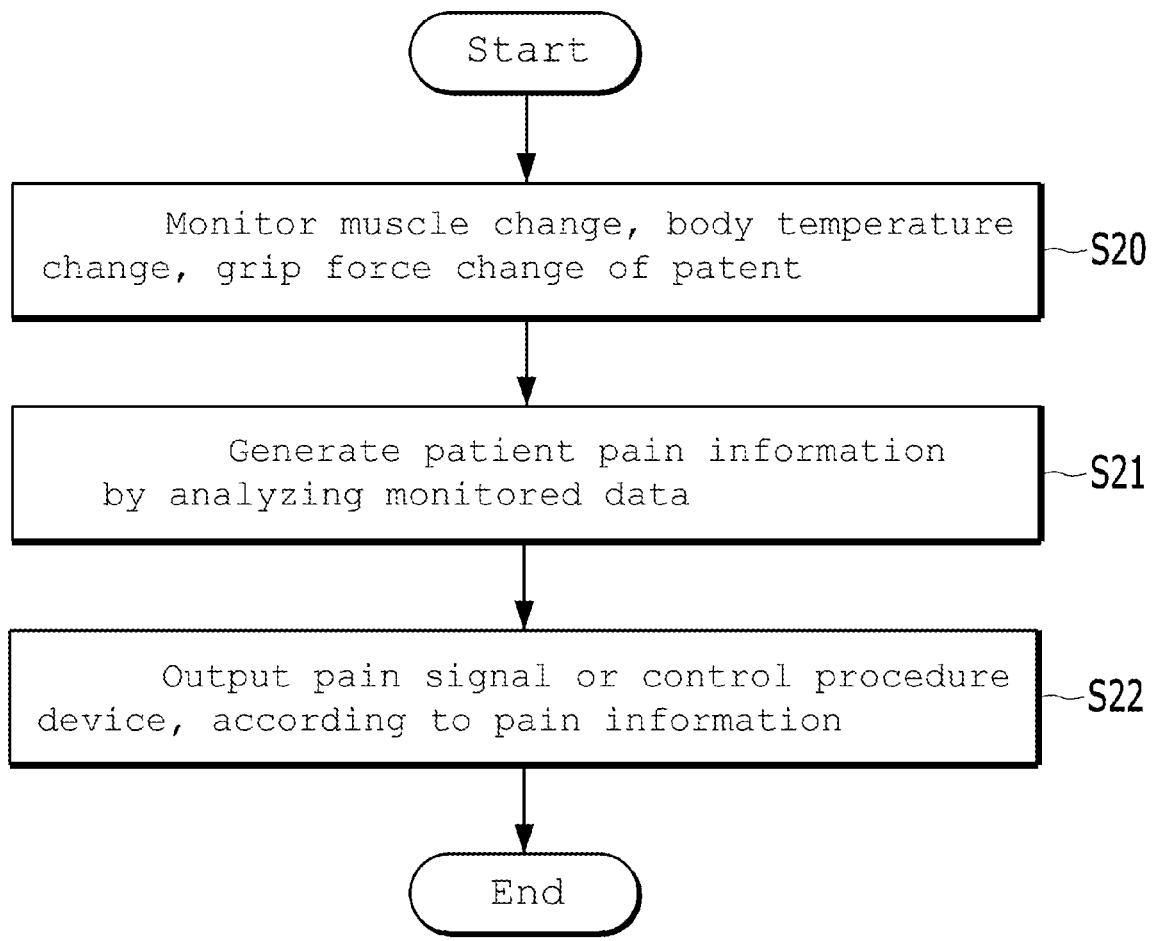
FIG. 2 is a flowchart for explaining a pain monitoring and feedback method for dental procedures according to an embodiment of the present invention.

FIG. 2 is a flowchart for explaining a pain monitoring and feedback method for dental procedures according to an embodiment of the present invention.

The patient's muscle change, body temperature change and grip force change is monitored in step S20.

To this end, the control unit 11 receives the monitoring data from the sensing device 14 through the communication unit 12 and analyzes the patient's change according to the progress of the procedure on the basis of a reference value before the occurrence of the pain so as to determine whether the patient feels pain. In addition, if the patient feels pain, the control unit 11 can analyze the degree of the pain that the patient feels.

The received monitoring data includes the image data of the patient photographed by the photographing unit 15. The control unit 11 analyzes the image of the patient, which is photographed before the procedure, so as to recognize the patient's muscle condition before the pain occurs and to set the same as a reference value for monitoring the muscle change. During the procedure, the image of the patient, which is periodically received, is analyzed to monitor how much it changes from the reference value. That is, in order to recognize the degree to which the muscle contracts instantaneously when the patient feels pain and frowns on the eyes or face or the patient's body becomes tense, patient behavior changes and muscle shape and size changes during such patient movement are analyzed from the patient's image.

In addition, the monitoring data includes the body temperature information of the patient detected by the heat-sensing unit 16. The control unit 11 receives the patient's body temperature information prior to the start of the procedure and sets the received patient's body temperature information as a reference value for monitoring the body temperature change. During the procedure, the periodically received body temperature information of the patient is analyzed to monitor how much it changes from the reference value.

Furthermore, the monitoring data includes the grip force information of the patient detected by the grip force-sensing unit 17. The control unit 11 receives the patient's grip force information prior to the start of the procedure and sets the received patient's grip force information as a reference value for monitoring the grip force change. During the procedure, the periodically received grip force information of the patient is analyzed to monitor how much it changes from the reference value.

In step S21, patient pain information is generated by analyzing the monitoring data.

The control unit 11 analyzes the data received from the photographing unit 15 and monitors the patient's muscle change in real time, thereby measuring the degree of muscle change. If the muscle change relative to the reference value exceeds the threshold value as the patient feels pain and thus moves his or her body, frowns on the face, or strains muscles, the control unit 11 generates pain information to inform such a change.

The threshold value for muscle change can be preset and can be changed by the user. For example, if the threshold value for muscle change is set to 5%, pain information is generated indicating that the patient has pain at the time when the muscle change is equal to or greater than 5%.

The control unit 11 analyzes the data received from the heat-sensing unit 16 and monitors the patient's body temperature change in real time, thereby measuring the degree of body temperature change. If the body temperature change relative to the reference value exceeds the threshold value as the patient feels pain and thus the patient's body temperature is increased, the control unit 11 generates pain information to inform such a change.

The threshold value for body temperature change can be preset and can be changed by the user. For example, if the threshold value for body temperature change is set to 0.5° C., pain information is generated indicating that the patient has pain at the time when the body temperature change is equal to or greater than 0.5° C. compared to that before the procedure.

The control unit 11 analyzes the data received from the grip force-sensing unit 17 and monitors the patient's grip force change in real time, thereby measuring the degree of grip force change. If the grip force change relative to the reference value exceeds the threshold value as the patient feels pain and thus grips the grip force-sensing unit 17 firmly, the control unit 11 generates pain information to inform such a change.

The threshold value for grip force change can be preset and can be changed by the user. For example, if the threshold value for grip force change is set to 30%, pain information is generated indicating that the patient has pain at the time when the grip force is increased by 30% or more compared to that before the procedure.

As described, reference values for muscle change, body temperature change, and grip force change can be set differently by patient depending on the data delivered prior to the patient's procedure. In addition, since the pain that each patient feels is subjective, threshold values for muscle change, body temperature change, and grip force change can also be set differently by patient.

In step S22, a pain signal is output according to the pain information or the procedure device 19 is controlled.

If at least one of the muscle change, the body temperature change, and the grip force change is equal to or greater than the threshold value, the control unit 11 outputs a pain signal by the output device 18 or a control signal to stop the dental procedure device 19.

The output device 18, which outputs a pain signal indicating that the patient feels pain more than the threshold value, is not limited to a specific device, and may be a monitor or a speaker connected to the computing device 10, a speaker disposed on or around a tool that the user uses during the procedure, a vibration device provided to an electronic device such as a dental drill, and the like, wherein a pain signal can be output in the form of a visual signal, a sound signal, a vibration signal, and the like. The user can recognize this signal and stop the procedure so that the user can respond to the patient's pain.

Meanwhile, the control unit 11 can output a control signal so as to pause the procedure device 19 when the patient shows change equal to or greater than the threshold value, thereby temporarily stopping the operation of the procedure device 19 and promptly responding to the patient's pain.

Depending on the setting of the user, both the output of the pain signal and the control of the procedure device 19 can be performed, or only one of them can be performed. For example, if it is determined that it is dangerous to stop intended dental procedures from time to time due to the patient's pain, it is possible to turn off the control function of the procedure device 19 and output only the pain signal. In this case, depending on the output of the pain signal, if the doctor recognizes the patient's pain according to the output of the pain signal, the procedure is manually stopped at a safe point.

Figure 3:
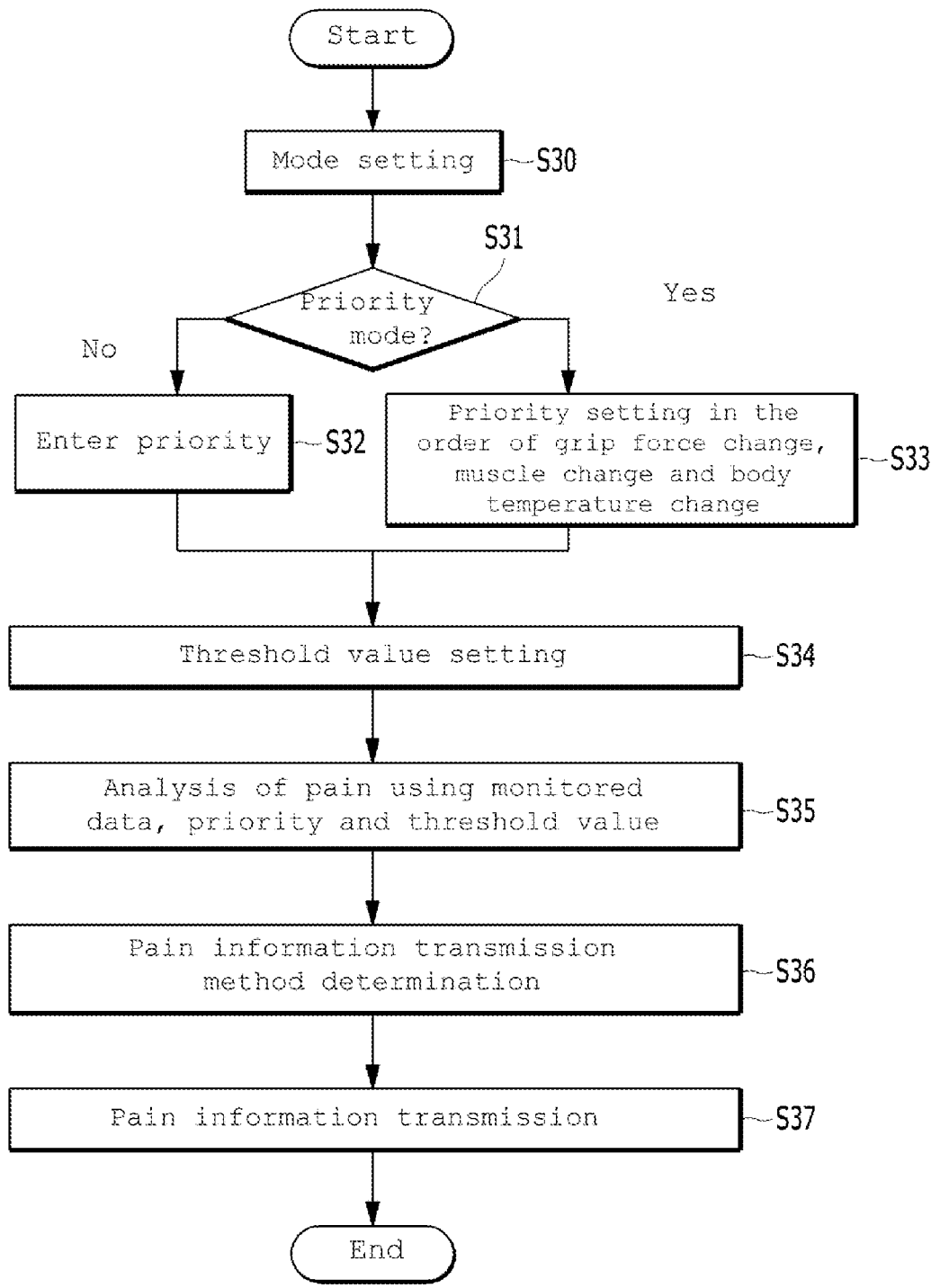
FIG. 3 is a flowchart illustrating an example of setting an operation mode and a threshold value in performing a pain monitoring and feedback according to an embodiment of the present invention.

FIG. 3 is a flowchart for explaining an example of setting an operation mode and a threshold value when performing a pain monitoring and feedback according to an embodiment of the present invention.

Referring to FIG. 3, the operation mode for determining priority of monitoring is set in step S30.

The operation mode is set to one of the priority mode and the normal mode and can be preset as a default value of the system or the setting thereof can be changed by the user.

In the present invention, information used for monitoring is the information on muscle change, the information on body temperature change, and the information on grip force change. Depending on the operation mode, which one of the three pieces of information is to be reflected first is determined.

In step S31, it is determined whether to operate in the priority mode or the normal mode according to the set mode information. The priorities to reflect muscle change, body temperature change, and grip force change in pain determination can be determined by other methods depending on whether to operate in priority mode or normal mode.

In the priority mode, the user can enter priorities of the information on muscle change, the information on body temperature change, and the information on grip force change (S32). It is based on the patient's tendency to decide which information will be reflected first to determine the pain.

For example, for a patient whose grip force is hardly changed or whose muscle change hardly occurs, priorities can be assigned such that body temperature change information is primarily monitored to analyze the pain. As another example, for a patient with a strong grip change and strong willingness to express pain with grip force, priorities can be assigned such that grip force change information is preferentially used.

The normal mode is the mode that can be used under normal circumstances, and the priorities are determined according to preset information in this normal mode (S33). For example, in the normal mode, priorities may be assigned such that the grip force change information, which reflects the patient's will to some extent, is monitored first, followed by the muscle change information and, finally, the body temperature change information.

In step S34, the threshold values for the patient's muscle change, body temperature change and grip force change are set. The threshold values can be set by using the set default value of the system according to the present invention or by the input or change made by the user. To this end, it is conceivable that an interface is required for the user to arbitrarily raise or lower the threshold values.

If all the three pieces of information are used for monitoring, a threshold value is set for each of muscle change, body temperature change and grip force change. If only one or two pieces of information are used according to priorities, only the threshold values for corresponding changes are set.

The threshold values can be set differently depending on the patient's tendency. For example, for a patient who continually interrupts the procedure by intentionally changing the grip force even with slight pain because of too much fear, the threshold value for the grip force change should be set high so that the procedure is stopped only when there is an extreme grip force change. In addition, for a patient with this tendency, it is conceivable to turn off the function of stopping the procedure and output a signal indicating that there is a pain, so that the doctor can recognize the pain and manually stop the procedure according to the doctor's option.

In step S35, it is determined whether the patient feels pain by analyzing the pain by using the monitoring data received from the sensing device 14, the priority and threshold value for each piece of information. Herein, determining that the patient feels pain means that the patient has pain exceeding the pain threshold value, of which pain the patient can tolerate. In other words, it is determined that the patient has significant pain such that it is necessary to inform the user of the same or stop the procedure.

According to the present invention, if any one of the three pieces of information has a large change instantaneously regardless of the operation mode, it is possible to analyze the pain by preferentially reflecting the corresponding information. For example, if the grip force increases instantaneously beyond the threshold value, you can determine that there is pain and control the procedure to stop immediately.

According to an embodiment of the present invention, a threshold value can be set for the average value of the changes corresponding to the three pieces of information. Herein, it can be determined that the patient feels significant pain when the average value of muscle change, body temperature change, and grip force change is equal to or higher than the threshold value.

In step S36, pain information transmission method is determined as to whether to output a notification signal, a control signal, or both the signals. The pain information transmission method can be set differently according to the user's experience, the type of procedures, the state or the tendency of the patent and the like.

In step S37, if it is determined that the patient's pain is equal to or higher than the preset pain threshold value, at least one of the notification signal for informing of the pain by the output device 18 and the control signal for stopping the dental procedure device 19 are output according to the pain information transmission method.

According to the present invention, it is possible to set a plurality of threshold values for the three pieces of information so as to treat pain through a plurality of divided steps. For example, a pain signal is output such that the user can recognize the pain if it is determined that there is the pain of level 1 by monitoring the three pieces of information, while immediately sending a control signal to the procedure device 19 so as to stop the procedure device 19 if it is determined that there is more severe pain of level 2.

The method according to an embodiment of the present invention may be implemented in the form of a program command which can be executed through various computer means and recorded in a computer-readable medium. The computer-readable medium may include program instructions, data files, data structures and the like, either alone or in combination. The program instructions recorded on the medium may be those specially designed and constructed for the present invention or may be available to those skilled in the art of computer software. Examples of computer-readable media include magnetic media such as hard disks, floppy disks, and magnetic tape, optical media such as CD-ROMs and DVDs, magneto-optical media such as floptical disks, and hardware devices specifically configured to store and execute program instructions such as ROM, RAM, flash memory and the like. Examples of program instructions include machine language code such as those produced by a compiler, as well as high-level language code that can be executed by a computer using an interpreter and the like.

Although the preferred embodiments of the present invention have been described above in detail, the present invention is not limited to the specific embodiments described above. That is, those skilled in the art will recognize that many changes and modifications can be made to the present invention without departing from the spirit and scope of the appended claims, and all such appropriate changes and modifications should be considered as equivalents falling within the scope of the present invention.

What is claimed is:

1. A pain monitoring and feedback system for dental procedures, comprising:
a sensing device including a photographing unit for taking a picture of a patient for the muscle change detection of the patient undergoing dental procedures, a heat-sensing unit for sensing the body temperature change of the patient, and a grip force-sensing unit for measuring the grip force of the patient; and
a computing device including a communication unit for receiving data from the sensing device and outputting a signal corresponding to pain information to the outside, a control unit for analyzing at least one of the muscle change, the body temperature change and the grip force change of the patient by using the monitoring data received via the communication unit so as to estimate the pain of the patient and outputting a pain signal or controlling a procedure device according to the estimated pain, and a memory for storing data necessary for processing the control unit,
wherein the control unit determines whether to operate in a priority mode or a normal mode according to set mode information, and determines priorities of the muscle change, the body temperature change, and the grip force change so as to reflect the muscle change, the body temperature change, and the grip force change in pain determination, the priorities being determined according to the input of a user in the case of operation in the priority mode and according to the preset information in the case of operation in the normal mode.

2. The pain monitoring and feedback system for dental procedures according to claim 1, wherein the control unit sets threshold values for the muscle change, the body temperature change, and the grip force change, and determines whether the pain of the patient is equal to or greater than a pain threshold value by using the data received by monitoring, the determined priorities, and the set threshold values.

3. The pain monitoring and feedback system for dental procedures according to claim 1, wherein when it is determined that the pain of the patient is equal to or greater than the preset pain threshold value, the control unit outputs at least one of a notification signal for informing of the pain by an output device and a control signal for stopping the dental procedure device.

4. A pain monitoring and feedback method for dental procedures, comprising the steps of:
receiving monitoring data from a photographing unit for taking a picture of a patient for the muscle change detection of the patient undergoing dental procedures, a heat-sensing unit for sensing the body temperature change of the patient, and a grip force-sensing unit for measuring the grip force of the patient;
analyzing at least one of the muscle change, the body temperature change and the grip force change of the patient by using the monitoring data so as to determine whether the pain of the patient is equal to or greater than a pain threshold value; and
outputting a pain signal according to the result of the determination or outputting a control signal for controlling a procedure device,
wherein the step of determining the pain comprises the steps of:
determining whether to operate in a priority mode or a normal mode according to set mode information; and
determining priorities of the muscle change, the body temperature change, and the grip force change so as to reflect the muscle change, the body temperature change, and the grip force change in pain determination, the priorities being determined according to the input of a user in the case of operation in the priority mode and according to the preset information in the case of operation in the normal mode.

5. The pain monitoring and feedback method for dental procedures according to claim 4, wherein the step of determining the pain further comprises the steps of:
setting threshold values for the muscle change, the body temperature change, and the grip force change; and
determining whether the pain of the patient is equal to or greater than a pain threshold value by using the data received by monitoring, the determined priorities, and the set threshold values.

6. The pain monitoring and feedback method for dental procedures according to claim 4, wherein the outputting step comprises the step of outputting at least one of a notification signal for informing of the pain by an output device and a control signal for stopping the dental procedure device, when it is determined that the pain of the patient is equal to or greater than the preset pain threshold value.

* * * * *